(12) United States Patent
Greiner et al.

(10) Patent No.: US 10,183,916 B2
(45) Date of Patent: Jan. 22, 2019

(54) PROCESS FOR THE PREPARATION OF TRIAZINES

(71) Applicant: DSM IP ASSETS B.V., Heerlen (NL)

(72) Inventors: Nadine Greiner, Kaiseraugst (CH); Sandro Schmid, Kaiseraugst (CH); René Tobias Stemmler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/571,113

(22) PCT Filed: May 12, 2016

(86) PCT No.: PCT/EP2016/060617
§ 371 (c)(1),
(2) Date: Nov. 1, 2017

(87) PCT Pub. No.: WO2016/184764
PCT Pub. Date: Nov. 24, 2016

(65) Prior Publication Data
US 2018/0170886 A1    Jun. 21, 2018

(30) Foreign Application Priority Data

May 18, 2015 (EP) .................................. 15167969

(51) Int. Cl.
| | |
|---|---|
| *C07D 251/24* | (2006.01) |
| *C07B 49/00* | (2006.01) |
| *C07B 63/00* | (2006.01) |
| *C07D 251/20* | (2006.01) |
| *C07F 3/02* | (2006.01) |

(52) U.S. Cl.
CPC ............ *C07D 251/24* (2013.01); *C07B 49/00* (2013.01); *C07B 63/00* (2013.01); *C07D 251/20* (2013.01); *C07F 3/02* (2013.01)

(58) Field of Classification Search
CPC .................................................. C07D 251/24
USPC ........................................................ 544/180
See application file for complete search history.

(56) References Cited

U.S. PATENT DOCUMENTS

| | | |
|---|---|---|
| 3,244,708 A | 4/1966 | Duennenberger et al. |
| 3,270,016 A | 8/1966 | Duennenberger et al. |
| 5,686,233 A | 11/1997 | Valet et al. |
| 5,955,060 A | 9/1999 | Hüglin et al. |

OTHER PUBLICATIONS

International Search Report for PCT/EP2016/060617, dated Jun. 30, 2016, 3 pages.

*Primary Examiner* — Kahsay Habte
(74) *Attorney, Agent, or Firm* — Nixon & Vanderhye P.C.

(57) ABSTRACT

The invention relates to an improved process for the manufacture of bis-resorcinyl triazines of formula (I) wherein $R^1$ is a $C_1$-$C_{18}$alkyl group or $C_2$-$C_{18}$alkenyl group as well as the respective alkyl substituted bis-resorcinyl derivatives of formula (II) wherein $R^1$ is a $C_1$-$C_{18}$alkyl group or $C_2$-$C_{18}$alkenyl group and $R^2$ and $R^3$ are independently of each other a $C_1$-$C_{18}$alkyl group or a $C_2$-$C_{18}$alkenyl group.

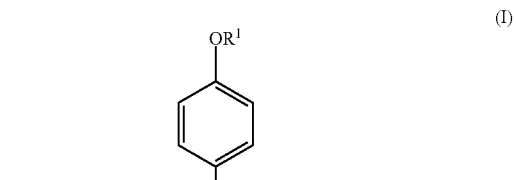

(I)

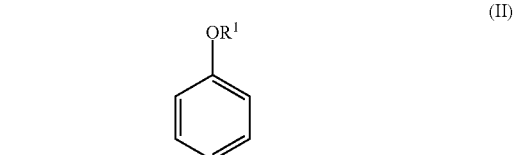

(II)

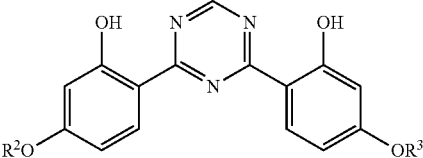

19 Claims, No Drawings

PROCESS FOR THE PREPARATION OF TRIAZINES

This application is the U.S. national phase of International Application No. PCT/EP2016/060617 filed 12 May 2016, which designated the U.S. and claims priority to EP Patent Application No. 15167969.3 filed 18 May 2015, the entire contents of each of which are hereby incorporated by reference.

The invention relates to an improved process for the manufacture of bis-resorcinyl triazines of formula (I) wherein $R^1$ is a $C_1$-$C_{18}$alkyl group or $C_2$-$C_{18}$alkenyl group as well as the respective alkyl substituted bis-resorcinyl derivatives of formula (II) wherein $R^1$ is a $C_1$-$C_{18}$alkyl group or $C_2$-$C_{18}$alkenyl group and $R^2$ and $R^3$ are independently of each other a $C_1$-$C_{18}$alkyl group or a $C_2$-$C_{18}$alkenyl group.

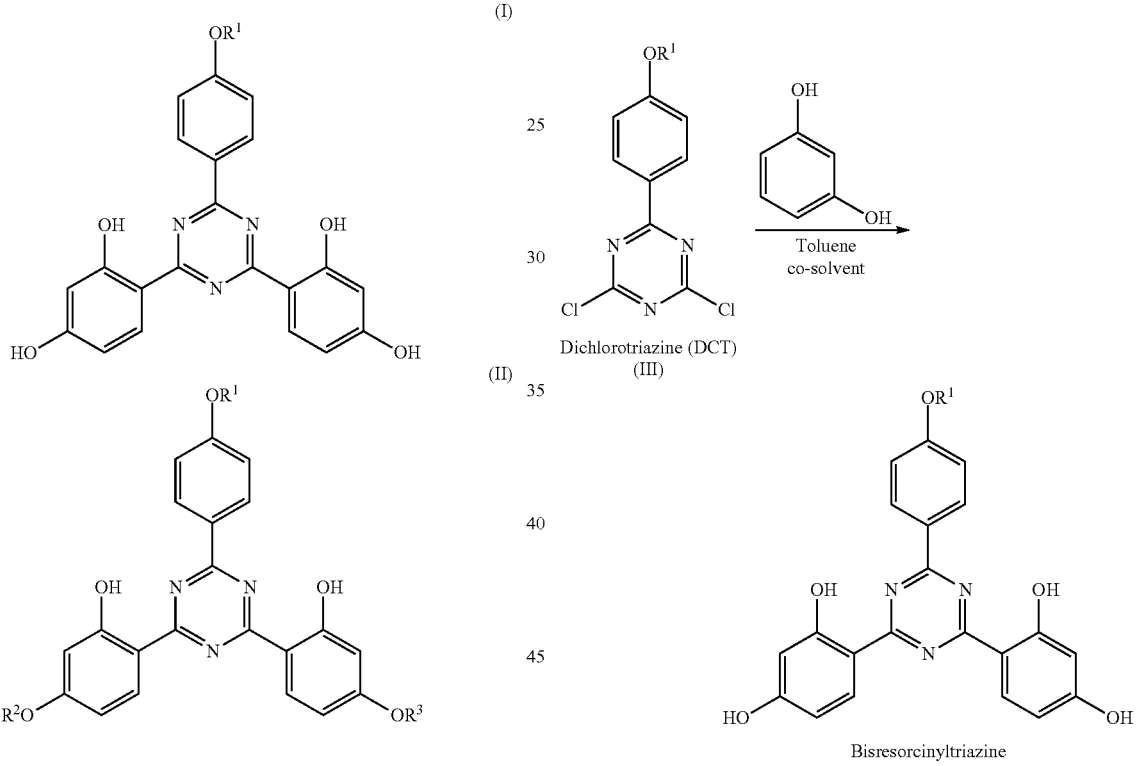

Bis-resorcinyl triazines of formula (I) are highly effective UV-absorbers which may, for example, be used as light stabilizers in plastics or as intermediates in the preparation of alkyl substituted bis-resorcinyl triazine derivatives of formula (II) such as for example Tinosorb® S [INCI Name: Bis-Ethylhexyloxyphenol Methoxyphenyl Triazine] which are particularly suitable as light screening agents in cosmetic products.

The preparation of bis-resorcinyl triazines of formula (I) and (II) is known and e.g. disclosed in U.S. Pat. No. 5,955,060. The preparation encompasses the reaction of cyanuric chloride with a phenyl magnesium bromide compound in a Grignard reaction to a dichlorotriazine. The two resorcinyl groups are then introduced by a Friedel-Crafts acylation with resorcinol in the presence of a Lewis acid, in particular an aluminum halide. In a third step, the etherification of the free 4-hydroxyl groups is carried out by alkylation.

Because of the continuously increasing demand for bis-resorcinyl triazines based light screening agents the object of the present invention was to provide a process for the preparation of bis-resorcinyl triazines derivatives which is easy to carry out and affords economic advantages as a result of high yields. Furthermore, the disadvantage that the Friedel-Crafts acylation often yields unwanted by-products which are hardly removable and are subsequently carried over to the bis-resorcinyl triazines of formula (II) should be avoided.

Thus, the objective of the present invention was to provide a process for the preparation of bis-resorcinyl triazines of formula (I) and (II) which is easy to carry out and affords economic and regulatory advantages as a result of higher yields and higher purities.

Thus in a first aspect the present invention relates to a process (A) for the preparation of bis-resorcinyl triazines of formula (I), said process comprising the step of reacting a solution of dichlorotriazine of formula (III) in toluene, wherein $R^1$ is a $C_1$-$C_{18}$alkyl group or a $C_2$-$C_{18}$ alkenyl group, with resorcinol in the presence of a Lewis acid and a co-solvent (Friedel-Crafts acylation), characterized in that the water content of the solution of the dichlorotriazine of formula (III) in toluene is less than 0.04 wt.-%, based on the total weight of the solution of the dichlorotriazine of formula (III) in toluene.

In the following, the dichlorotriazine of formula (III) is referred to as 'DCT' (DiChloroTriazine) and the solution thereof in toluene as 'DCT-toluene solution'.

In a preferred embodiment the water content of the DCT-toluene solution is less than 0.03 wt.-%, more preferably the water content of the DCT-toluene solution is less than 0.025 wt.-%, most preferably equal or less than 0.02 wt.-%, based on the total weight of the DCT-toluene solution.

Examples of $C_1$-$C_{18}$ alkyl groups or $C_2$-$C_{18}$ alkenyl groups are branched or unbranched alkyl, respectively alkenyl groups such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, ethenyl, 2-propenyl and 3-butenyl groups.

In a preferred embodiment $R^1$ is a $C_1$-$C_5$ alkyl group, more preferably a $C_1$-$C_2$ alkyl group, most preferably a methyl group.

The term co-solvents as used herein refers to chemicals characterized by their ability to be miscible with toluene. Particular suitable co-solvents in all embodiments of the present invention encompass sulfolane, benzonitrile, chlorobenzene, nitrobenzene, acetonitrile and pivalonitrile as well as mixtures thereof. In all embodiments of the present invention it is preferred that only one co-solvent is used. Preferably the one co-solvent is selected from the group consisting of nitrobenzene, pivalonitrile and benzonitrile. Most preferably the co-solvent is nitrobenzene or benzonitrile as this leads to particular high yields.

Suitable Lewis acids encompass aluminum halides as well as magnesium halides. In all embodiments of the present invention the preferred Lewis acid is aluminum trichloride ($AlCl_3$).

In a particular advantageous embodiment, the invention encompasses a process (B), which is a process (A) wherein $R^1$ is a methyl group, the co-solvent is benzonitrile and the Lewis acid is aluminum trichloride.

In all embodiments of the present invention, the amount of resorcinol is at least 2 mol-equivalents with respect to the dichlorotriazine of formula (III). Preferably, a slight excess of resorcinol is used. Most preferably the amount of resorcinol is selected in the range of 2 to 2.5 mol-equivalents, with respect to the dichlorotriazine of formula (III).

In all embodiments of the present invention, the amount of the co-solvent is preferably selected in the range of 0.5 to 10, more preferably in the range of 1 to 6, most preferably in the range of 2 to 5 mol-equivalents, with respect to the dichlorotriazine of formula (III).

In all embodiments of the present invention, the amount of the Lewis acid is preferably selected in the range of 0.5 to 7, more preferably in the range of 0.75 to 5, most preferably in the range of 1 to 3 mol-equivalents, with respect to the dichlorotriazine of formula (III).

In all embodiments of the invention, the reaction temperature of the Friedel-Crafts acylation is preferably selected in the range of 25 C to 100° C. such as more preferably in the range of 50° C. to 70° C. and most preferably in the range of 55° to 65° C. (at atmospheric pressure). It is well understood that the reaction temperature would have to be adjusted accordingly if pressure/vacuum is applied in the process according to the present invention, which however can easily be adjusted by a person skilled in the art and is encompassed herein as well.

Thus, in another particular advantageous embodiment, the invention encompasses a process (C), which is a process (B), wherein the amount of the co-solvent is selected in the range of 2 to 5 mol-equivalents with respect to the dichlorotriazine of formula (III), the amount of Lewis acid is selected in the range of 1 to 3 mol-equivalents with respect to the dichlorotriazine of formula (III) and the reaction temperature is selected in the range of 55° to 65° C. (at atmospheric pressure).

It is furthermore preferred that the amount of dichlorotriazine of formula (III) in the DCT-toluene solution used in the processes according to the present invention is selected in the range of 5 to 25 wt.-%, preferably in the range of 10 to 20 wt.-%, most preferably in the range of 12 to 17 wt.-%, based on the total weight of the DCT-toluene solution.

Thus, in a very advantageous embodiment the invention encompasses a process (D) which is a process (C), wherein the DCT-toluene solution has a DCT content in the range of 5 to 25 wt.-%, preferably in the range of 10 to 20 wt, based on the total weight of the DCT-toluene solution.

The DCT-toluene solution having a water content as specified herein can be prepared by dissolving a dichlorotriazine of formula (III) in dry toluene (e.g. Toluene puriss. p.a., ACS reagent, ≥99.7% (GC) commercially available from Sigma-Aldrich) according to procedures well known to a person skilled in the art. Preferably, the dichlorotriazine of formula (III) used for preparing the solution has a purity (GC) of ≥90%, preferably of ≥94%, most preferably of ≥98%. If necessary the dichlorotriazine of formula (III) can be dried by vacuum-drying before dissolution according to standard methods in the art. A particular suitable dichlorotriazine of formula (III) which can be used for preparing the DCT-toluene solution according to the present invention is 2,4-Dichloro-6-(4-methoxyphenyl)-1,3,5-triazine [CAS 90723-86-7] having a purity (GC) of ≥94%, which is e.g. commercially available at Aldlab Chemical Building Blocks.

Alternatively and preferably, the solution of dichlorotriazine of formula (III) in toluene (DCT-toluene solution) is, however, prepared by a process (E) comprising the subsequent steps of (i) Grignard reaction of cyanuric chloride with a 4-alkoxyphenylmagnesium halide of formula (IV)

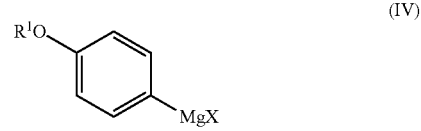

(IV)

wherein $R^1$ is a $C_1$-$C_{18}$ alkyl group or a $C_2$-$C_{18}$ alkenyl group and
X is Cl, Br or I
in tetrahydrofuran (THF) to yield a dichlorotriazine of formula (III), followed by
(ii) solvent exchange of THF with toluene resulting in the DCT-toluene solution, followed by
(iii) washing of the DCT-toluene solution with aqueous hydrochloric acid, followed by
(iv) phase separation and optionally a pre-drying of the DCT-toluene solution with a drying agent, followed by
(v) co-evaporation of the washed and optionally pre-dried DCT-toluene solution with toluene until a water content of less than 0.04 wt.-%, preferably less than 0.03 wt.-%, more preferably less than 0.025 wt.-%, most preferably equal or less than 0.02 wt.-% and a THF content of less than 3 wt.-%, preferably less than 2.5 wt.-%, most preferably less than 2 wt.-%, based on the total weight of the DCT-toluene solution is obtained.

In a particular advantageous embodiment, the DCT-toluene solution used in the process according to the invention has a water content of less than 0.04 wt.-% and a THF content of less than 3 wt.-%, more preferably a water content of less than 0.03 wt.-%, and a THF content of less than 2.5 wt.-% and most preferably a water content of less than 0.025 wt.-%, and a THF content of less than 2 wt.-%, such as a water content equal or less than 0.02 wt.-% and a THF content of less than 2 wt.-, based on the total weight of the DCT-toluene solution.

The drying agent in step (iv) can be selected from conventional drying agents commonly used in the organic laboratories such as the anhydrous forms of calcium chloride ($CaC_2$), sodium sulfate ($Na_2SO_4$) calcium sulfate ($CaSO_4$ (as Drierite)) and magnesium sulfate ($MgSO_4$) as well as mixtures thereof. Preferably the drying agent is sodium sulfate ($Na_2SO_4$) or magnesium sulfate ($MgSO_4$).

In a very advantageous embodiment the invention encompasses a process (F), which is a process (D), wherein the DCT-toluene solution is prepared according to the process (E).

The water content ≥0.1 wt.-% as well as the THF content of the DCT-toluene solution of this invention is to be understood as determined by GC-TCD (i.e. a GC connected to a thermal conductivity detector). Water contents ≤0.1 wt.-% are determined by coulometric Karl-Fischer titration, as the latter method has a lower limit of quantification.

A particular advantageous 4-$C_1$-$C_{18}$alkoxyl- or $C_2$-$C_{18}$ alkenyloxyphenylmagnesium halogenide to be used in the Grignard reaction according to the present invention is 4-methoxyphenylmagnesium bromide, which can be prepared from 4-bromoanisol and magnesium turnings in THF according to standard methods in the art or is e.g. commercially available from Sigma-Aldrich (CAS 13139-86-1, 0.5 M in THF).

As aqueous hydrochloric acid preferably 1N HCl is used.

In a further embodiment, the process according to the present invention comprises a subsequent alkylation step of the bis-resorcinyl triazines of formula (I) with a $C_1$-$C_{18}$alkyl or $C_2$-$C_{18}$ alkenyl halogenide to obtain the respective alkyl substituted bis-resorcinyl derivatives of formula (II). Preferably a $C_3$-$C_{10}$alkyl halogenide, more preferably a $C_3$-$C_{10}$alkyl halogenide and most preferably ethylhexyl halogenide is used. In a most preferred embodiment the bis-resorcinyl derivatives of formula (II) wherein $R^1$ is a methyl group and $R^2$ and $R^3$ are a ethylhexyl groups is prepared according to the process of the present invention. The alkylation can be done according to standard methods in the art e.g. by etherification of a bis-resorcinyl triazines of formula (I) with an ethylhexyl halogenide such as 3-bromoethylhexane or 3-chloroethylhexane in the presence of a base as e.g. outlined in U.S. Pat. No. 5,955,060 examples 1 and 2.

Each reaction of the process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

Experimental Part

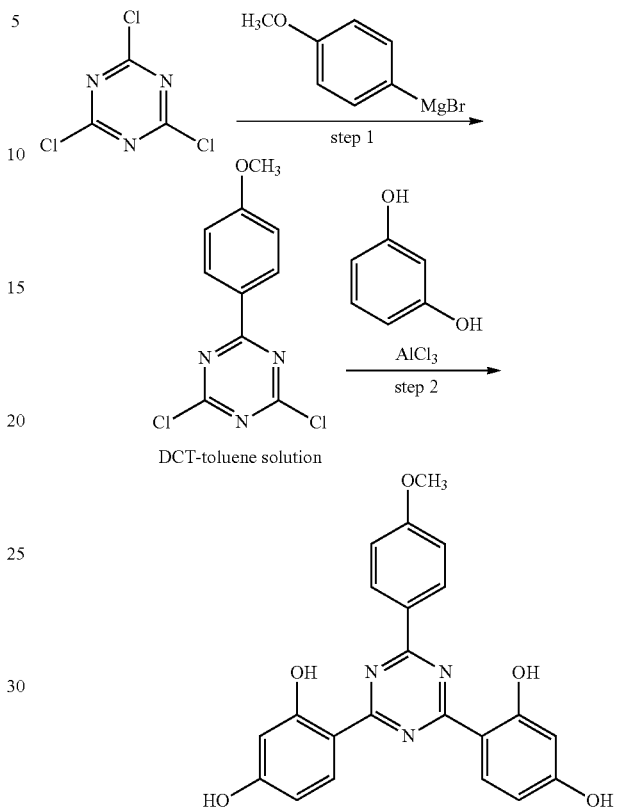

Step 1: Synthesis of
2,4-dichloro-6-(4-methoxyphenyl)-1,3,5-triazine
toluene Solution In a 500 mL 4-necked flask equipped with argon inlet, mechanical stirrer, reflux condenser, thermometer and addition funnel, 11.90 g magnesium turnings (0.488 mol, 1.20 eq) and a few grains of iodine were suspended in 130 mL dry THF. Under dry protective gas (nitrogen or argon) 5% of a solution of 92.2 g 4-bromoanisol (61.7 mL, 0.488 mol, 1.20 eq.) in 116 mL dry THF was added. An exothermic reaction indicated the start of the Grignard reaction, after which the remaining solution of 4-bromoanisol was added slowly. After complete addition and dissolution of the magnesium turnings, the jacketed reactor was heated to 70° C. and stirred for 2-4 h until all magnesium turnings dissolved and full conversion of 4-bromoanisol was observed (by GC analysis).

The resulting Grignard solution was then added dropwise at 0-5° C. to a suspension of 74.9 g cyanuric chloride (0.407 mol, 1.0 eq.) in 103 mL dry THF. After complete addition, the reactor was warmed to 25° C. and the reaction mixture was stirred for another 30 min. Then, vacuum was applied (~300 mbar) and the reactor was heated to 50° C. in order to distill off about 140 ml of THF. Subsequently, 700 mL of toluene was added continuously while distilling off a mixture of THF/toluene. Then 500 mL 1N HCl was added slowly. The phases were separated, furnishing 707 g of a solution of 2,4-dichloro-6-(4-methoxyphenyl)-1,3,5-triazine (DCT/M) in toluene (approx. 14.7 wt % DCT/M).

The water, respectively THF content of the resulting DCT/M-toluene solutions obtained as outlined above was adjusted by further co-evaporation with dry toluene (Fluka, puriss. P.A. ACS reagent) resulting in the DCT/M-toluene solutions as outlined in table 1, which were used in the subsequent reaction step 2.

TABLE 1

Solutions of 2,4-dichloro-6-(4-methoxyphenyl)-1,3,5-triazine in toluene (DCT/M-toluene solutions)

| Example | DCT/M [wt.-%] | THF [wt.-%] | $H_2O$ [wt.-%] |
|---|---|---|---|
| Ref 1 | 14.7 | 5.7 | 0.07 |
| Ref 2 | 14.7 | 5.8 | 0.17 |
| Ref 3 | 14.7 | 6.0 | 0.17 |
| Ref 4 | 14.7 | 1.2 | 0.06 |
| 1 | 14.7 | 2.0 | 0.02 |
| 2 | 14.7 | None | 0.02 |

The THF and $H_2O$ content was determined by GC-TCD. A $H_2O$ content below 0.1 wt.-% was additionally analyzed by coulometric Karl-Fischer titration.

Step 2: Synthesis of 4,4'-[6-(4-methoxyphenyl)-1,3,5-triazine-2,4-diyl]-bis-1,3-benzenediol In a 1.5 L glass reactor with argon inlet mechanical stirrer, reflux condenser, thermometer and an off-gas connection to a NaOH, 94 g of resorcinol (0.857 mol, 2.1 eq. with respect to DCT/M) and 3.2 mol eq. of benzonitrile (with respect to DCT/M) were added to 707 g of the respective solution of DCT/M in toluene as outlined in table 1. The resulting solution was heated to 60° C. Then 112 g $AlCl_3$ (0.842 mol, 2.07 eq. with respect to DCT/M) was added in portions. After complete addition the reaction was kept at 60° C. for approx. 4 h. Upon full conversion heating was stopped. Then 55 mL 1N HCl (55 mmol) was added dropwise, followed by 150 mL toluene, 165 mL 1N HCl (165 mmol) and 150 mL of water. The resulting suspension was filtered and subsequently washed with 350 mL toluene and 1000 mL of water. The filter cake was sucked dry and then dried under vacuum (~100 mbar) at 60° C. overnight, furnishing the indicated yield of 4,4'-[6-(4-methoxyphenyl)-1,3,5-triazine-2,4-diyl]-bis-1,3-benzenediol (MTB).

TABLE 2

Comparison of yields and impurities using DCT/M-toluene solutions having different $H_2O$/THF contents

| Example | DCT/M solution used | Impurity MW 311 [wt %] | Yield* MTB [wt %] |
|---|---|---|---|
| Ref 5 | Ref 1 | 2.30 | 73 |
| Ref 6 | Ref 2 | 2.41 | 71 |
| Ref 7 | Ref 3 | 2.19 | 63 |
| Ref 8 | Ref 4 | 0.71 | 76 |
| 3 | 1 | 0.13 | 81 |
| 4 | 2 | 0.29 | 84 |

*based on cyanuric chloride

As can be retrieved from table 2, the yield of the 2,4-dichloro-6-(4-methoxyphenyl)-1,3,5-triazine (compound of formula (I) wherein $R^1$ is a methyl group) is significantly increased by reducing the water as well as the THF content in the DCT/M-solution. Furthermore, the impurity with a molecular weight of 311 g/mol (impurity MW 311) was significantly reduced.

Example 4 as outlined above was repeated by replacing toluene in example 1 by xylene and benzonitrile by sulfolane (Ref 9), respectively by replacing benzonitrile by a different co-solvent (examples 5, 7 and 8) as outlined in table 3.

TABLE 3

Comparison different solvents/co-solvents

| | DCT/M-solvent solution (14.7 wt.-%) | | | | |
|---|---|---|---|---|---|
| Example | Solvent | Water [ppm] | THF [ppm] | Co-solvent | Yield* MTB [wt %] |
| Ref 9 | xylene | 0.028 | None | sulfolane | 74 |
| 5 | toluene | 0.022 | None | sulfolane | 78 |
| 6 | toluene | 0.020 | None | benzonitrile | 84 |
| 7 | toluene | 0.022 | None | nitrobenzene | 87 |
| 8 | toluene | 0.035 | None | pivalonitrile | 80 |

*based on cyanuric chloride

As can be retrieved from table 3, the use of toluene led to an increase of the overall isolated yield. Furthermore, the use of benzonitrile, nitrobenzene respectively pivalonitrile as co-solvent is particularly advantageous.

The invention claimed is:
1. A process for preparing bis-resorcinyl triazines of formula (I):

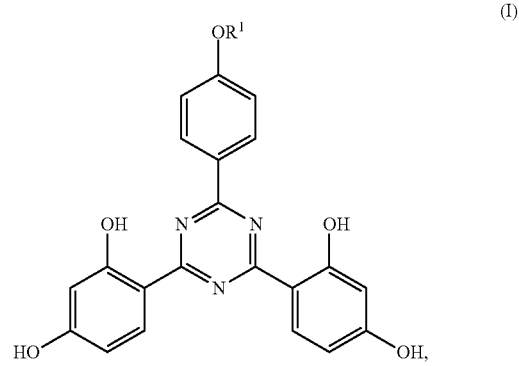

where $R^1$ is a $C_1$-$C_{18}$ alkyl group or a $C_2$-$C_{18}$ alkenyl group, wherein
the process comprises a the step of reacting resorcinol with a dichlorotriazine-toluene (DCT-toluene) solution comprised of dichlorotriazine of formula (III):

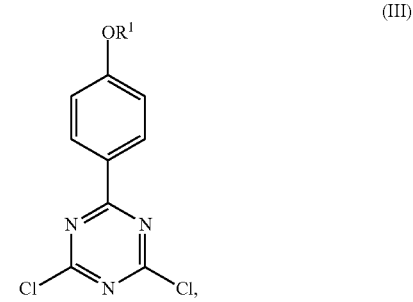

where $R^1$ is as defined previously, and toluene in the presence of a Lewis acid and a co-solvent, wherein the Lewis acid is selected from the group consisting of aluminum halides and magnesium halides, and wherein the co-solvent is selected from the group consisting of sulfolane, benzonitrile, chlorobenzene, nitrobenzene, acetonitrile, pivalonitrile and mixtures thereof, and wherein the DCT-toluene solution has a water content which is less than 0.04 wt.-%, based on the total weight of the DCT-toluene solution.

2. The process according to claim 1, wherein the water content of the DCT-toluene solution is less than 0.03 wt.-%, based on the total weight of the DCT-toluene solution.

3. The process according to claim 1, wherein the water content of the DCT-toluene solution is less than 0.025 wt.-%, based on the total weight of the DCT-toluene solution.

4. The process according to claim 1, wherein $R^1$ in formulas (I) and (III) is a $C_1$-$C_2$alkyl group.

5. The process according to claim 4, wherein $R^1$ is a methyl group.

6. The process according to claim 1, wherein the Lewis acid is aluminum trichloride.

7. The process according to claim 1, wherein the co-solvent is selected from the group consisting of benzonitrile, nitrobenzene and pivalonitrile.

8. The process according to claim 1, wherein the dichlorotriazine of formula (III) is present in the DCT-toluene solution in an amount of 5 to 25 wt.-%, based on the total weight of the DCT-toluene solution.

9. The process according to claim 1, wherein the DCT-toluene solution is prepared by the sequential steps of:

(i) conducting a Grignard reaction of cyanuric chloride with a 4-alkoxyphenylmagnesium halide of formula (IV):

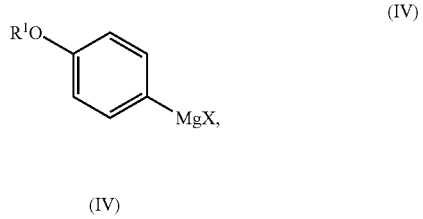

(IV)

where $R^1$ is a $C_1$-$C_{18}$alkyl group or a $C_2$-$C_{18}$ alkenyl group, and X is Cl, Br or I, in tetrahydrofuran (THF) to yield the dichlorotriazine of formula (III), (ii) conducting a solvent exchange of THF with toluene resulting in the DCT-toluene solution, followed by (iii) washing of the DCT-toluene solution with aqueous hydrochloric acid, (iv) conducting phase separation and optionally a pre-drying of the DCT-toluene solution with a drying agent, and (v) conducting co-evaporation of the washed DCT-toluene solution to achieve a water content of the DCT-toluene solution which is less than 0.04 wt.-%, and a THF content of less than 3 wt.-%, based on the total weight of the DCT-toluene solution.

10. The process according to claim 9, wherein step (v) is practiced to obtain a THF content in the DCT-toluene solution of less than 3 wt.-%, based on the total weight of the DCT-toluene solution.

11. The process according to claim 9, wherein step (v) is practiced to obtain a water content in the DCT-toluene solution of less than 0.03 wt.-% and a THF content in the DCT-toluene solution of less than 2 wt.-%, based on the total weight of the DCT-toluene solution.

12. The process according to claim 9, wherein the 4-alkoxyphenylmagnesium halide is 4-methoxyphenylmagnesium bromide.

13. The process according to claim 9, wherein the drying agent is selected from the group consisting of the anhydrous forms of calcium chloride, sodium sulfate, calcium sulfate, magnesium sulfate and mixtures thereof.

14. The process according to claim 1, which further comprises etherifying the bis-resorcinyl triazine of formula (I) with an alkylhalogenide in the presence of a base.

15. The process according to claim 14, wherein the alkylhalogenide is 3-bromoethylhexane or 3-chloroethylhexane.

16. The process according to claim 9, wherein step (v) is practiced to obtain a water content in the DCT-toluene solution of less than 0.03 wt.-%, and a THF content in the DCT-toluene solution of less than 2.5 wt.-%, based on the total weight of the DCT-toluene solution.

17. The process according to claim 9, wherein step (v) is practiced to obtain a water content in the DCT-toluene solution of less than 0.025 wt.-%, and a THF content in the DCT-toluene solution of less than 2 wt.-%, based on the total weight of the DCT-toluene solution.

18. The process according to claim 17, wherein the water content of the DCT-toluene solution is equal to or less than 0.02 wt.-%, based on the total weight of the DCT-toluene solution.

19. The process according to claim 1, wherein the water content of the DCT-toluene solution is equal to or less than 0.02 wt.-%, based on the total weight of the DCT-toluene solution.

* * * * *